(12) United States Patent
Kavlick et al.

(10) Patent No.: US 9,765,400 B2
(45) Date of Patent: Sep. 19, 2017

(54) QUANTIFICATION OF HUMAN MITOCHONDRIAL DNA USING SYNTHESIZED DNA STANDARDS

(71) Applicant: Federal Bureau of Investigation, Washington, DC (US)

(72) Inventors: Mark Francis Kavlick, King George, VA (US); Bruce Budowle, North Richland Hills, TX (US)

(73) Assignee: The United States of America as represented by the Federal Bureau of Investigation, Dept. of Justice, Washington, DC (US)

( * ) Notice: Subject to any disclaimer, the term of this patent is extended or adjusted under 35 U.S.C. 154(b) by 336 days.

(21) Appl. No.: 14/729,387

(22) Filed: Jun. 3, 2015

(65) Prior Publication Data

US 2015/0322525 A1  Nov. 12, 2015

Related U.S. Application Data

(62) Division of application No. 13/436,277, filed on Mar. 30, 2012, now Pat. No. 9,080,205.

(51) Int. Cl.
*C12Q 1/68* (2006.01)

(52) U.S. Cl.
CPC ......... *C12Q 1/6883* (2013.01); *C12Q 1/6851* (2013.01); *C12Q 2545/101* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,933,120 B2 | 8/2005 | Seidman | |
| 7,267,946 B2 | 9/2007 | Runge | |
| 7,285,631 B2 | 10/2007 | Bejanin | |
| 7,476,733 B2 | 1/2009 | Carvalho | |
| 2003/0099933 A1 | 5/2003 | Cote | |
| 2005/0214820 A1 | 9/2005 | Cote | |
| 2006/0051787 A1 | 3/2006 | Kim | |
| 2006/0099620 A1 | 5/2006 | Walker | |
| 2009/0181367 A1 | 7/2009 | Cote | |

FOREIGN PATENT DOCUMENTS

WO  0164835 A1  9/2001

OTHER PUBLICATIONS

Swango, K.L. et al., "A Quantitative PCR Assay for the Assessment of DNA Degradation in Forensic Samples," Forensic Sci. Int. 158(1): 14-26 (2006) (e-pub. Jun. 3, 2005).

Timken, M.D. et al., "A Duplex real-time qPCR Assay for the Quantification of Human Nuclear and Mitochondrial DNA in Forensic Samples: Implications for Quantifying DNA in Degraded Samples," J. Forensic Sci. 50(5): 1044-60 (Sep. 2005).
DeMerida, A.M.P. et al., "Mitochondrial DNA Variation Among Anopheles Albimanus Populations," Am. J. Trop. Med. Hyg. 61(2): 230-239 (1999).
Li, F.J. et al., "PCR approach for the detection of Trypanosoma brucei and T. equiperdum and their differentiation from T. evansi based on maxicircle kinetoplast DNA," Mol. Cell. Probes 21(1): 1-7 (Feb. 2007) (e-pub May 9, 2006).
Caldwell, J.M. et al., "Mitochondrial multiplex real-time PCR as a source tracking method in fecal-contaminated effluents," Environ. Sci. Technol. 41(9): 3277-83 (May 1, 2007).
Ballinger, S.W. et al., "Mitochondrial Genome Damage Associated with Cigarette Smoking," Cancer Research 56: 5692-97 (Dec. 15, 1996).
Bai, R.K. et al., "Quantitative PCR analysis of mitochondrial Dna content in patients with mitochondrial disease," Ann. N.Y. Acad. Sci. 1011: 304-09 (Apr. 2004).
Timken, M.D. et al., "Quantitation of DNA for Forensic DNA Typing by qPCR," Final Report: NIJ Award# 2002-IJ-CX-K008 (Jun. 2005).
Roby, R.K. et al., "Development of an Integrated Workflow from Laboratory Processing to Report Generation for mtDNA Haplotype Analysis," NIJ Cooperative Agreement 2008-DNA-BX-K192 (Apr. 2011).
Kavlick, M.F. et al., "Quantification of Human Mitochondrial DNA Using Synthesized DNA Standards," J. Forensic Sci. 56(6): 1457-1463 (Nov. 2011) (e-pub Sep. 2, 2011).
Fisher, C., "mtDNA qPCR Assay," presentation for 2009 FBI Regional mtDNA Program Workshop, New Jersey State Police, presented May 12, 2009.
Kavlick, M.F. et al., "Real-Time Quantitative PCR Assay for Quantification of Mitochondrial DNA," Poster, presented Oct. 2008.
Kavlick, M.F., "Real-Time Quantitative PCR Assay for Mitochondrial DNA Quantification," presentation for American Academy of Forensic Sciences, presented Feb. 20, 2009.
Sarkar, M. et al., FEBS Letters 579, 3449-3460 (Jun. 2005).
Hofhaus, G. et al., Mol. Cell. Biol. 15(2): 964-974 (1995).
von Wurmb-Schwark, N. et al., Forensic Sci. Int. 126: 34-39 (2002).
Lowe, T. et al., Nucleic Acids Research 18(7): 1757-1761 (1990).

*Primary Examiner* — Stephanie K Mummert
(74) *Attorney, Agent, or Firm* — Kristin K. Vidovich

(57) ABSTRACT

A real-time quantitative PCR assay that utilizes a duplex, synthetic DNA standard to ensure optimal quality assurance and quality control. One embodiment of the invention facilitates amplification of mtDNA by focusing on a 105-base pair target sequence that is minimally homologous to non-human mtDNA. The present invention can also be used to identify the presence of PCR inhibitors and thus indicate the need for sample repurification.

1 Claim, 9 Drawing Sheets

```
13261 caactaggac tcataatagt tacaatcggc atcaaccaac cacacctagC ATTCCTGCAC
13321 ATCTGtaccc acgccttctt caagccata ctatttatgt gctccgggtc catcatccac
13381 aaccttaaca atgaacaaga tattcgataa ataggaggac tactcaaaac cataccictc
```

Signature  
Sequence gcc ata       taa cga  
::: :::  ⇒  ::: :::  
cgg tat       att gca Ala Met       Och Arg

Figure 7

SEQUENCE LISTING

<160> NUMBER OF SEQ ID NOS: 9

<210> SEQ ID NO 1
<211> LENGTH: 115
<212> TYPE: DNA
<213> ORGANISM: Artificial Sequence
<220> FEATURE:
<223> OTHER INFORMATION: qPCR Standard (forward strand)

<400> SEQUENCE: 1

```
caatcggcat caaccaacca cacctagcat tcctgcacat ctgtacccac gccttcttca      60
aataacgact atttatgtgc tccgggtcca tcatccacaa ccttaacaat gaaca           115
```

<210> SEQ ID NO 2
<211> LENGTH: 115
<212> TYPE: DNA
<213> ORGANISM: Artificial Sequence
<220> FEATURE:
<223> OTHER INFORMATION: qPCR standard (reverse strand)

<400> SEQUENCE: 2

```
tgttcattgt taaggttgtg gatgatggac ccggagcaca taaatagtcg ttatttgaag      60
aaggcgtggg tacagatgtg caggaatgct aggtgtggtt ggttgatgcc gattg           115
```

<210> SEQ ID NO 3
<211> LENGTH: 21
<212> TYPE: DNA
<213> ORGANISM: Artificial Sequence
<220> FEATURE:

<223> OTHER INFORMATION: Foward Primer

<400> SEQUENCE: 3
ggcatcaacc aaccacacct a                                              21

<210> SEQ ID NO 4
<211> LENGTH: 24
<212> TYPE: DNA
<213> ORGANISM: Artificial Sequence
<220> FEATURE:
<223> OTHER INFORMATION: Reverse Primer

<400> SEQUENCE: 4
attgttaagg ttgtggatga tgga                                           24

<210> SEQ ID NO 5
<211> LENGTH: 16
<212> TYPE: DNA
<213> ORGANISM: Artificial Sequence
<220> FEATURE:
<223> OTHER INFORMATION: Probe

<400> SEQUENCE: 5
cattcctgca catctg                                                    16

<210> SEQ ID NO 6
<211> LENGTH: 20
<212> TYPE: DNA
<213> ORGANISM: Artificial Sequence
<220> FEATURE:
<223> OTHER INFORMATION: HVR1 Forward Primer

<400> SEQUENCE: 6
caccattagc acccaaagct                                                20

<210> SEQ ID NO 7
<211> LENGTH: 20
<212> TYPE: DNA
<213> ORGANISM: Artificial Sequence
<220> FEATURE:
<223> OTHER INFORMATION: HVR1 Reverse Primer

<400> SEQUENCE: 7
gaggatggtg gtcaagggac                                                20

<210> SEQ ID NO 8
<211> LENGTH: 20
<212> TYPE: DNA
<213> ORGANISM: Artificial Sequence
<220> FEATURE:
<223> OTHER INFORMATION: HVR2 Forward Primer

<400> SEQUENCE: 8
ctcacgggag ctctccatgc                                                20

<210> SEQ ID NO 9
<211> LENGTH: 21
<212> TYPE: DNA
<213> ORGANISM: Artificial Sequence
<220> FEATURE:
<223> OTHER INFORMATION: HVR2 Reverse Primer

<400> SEQUENCE: 9
ctgttaaaag tgcataccgc c                                              21

QUANTIFICATION OF HUMAN MITOCHONDRIAL DNA USING SYNTHESIZED DNA STANDARDS

STATEMENT REGARDING FEDERALLY SPONSORED RESEARCH OR DEVELOPMENT

The claimed invention was developed by an agency of the United States Government; the federal government therefore has certain rights in the invention.

SEQUENCE LISTING

The sequence listing in electronic format is provided as a file entitled "sequence_listing_ST25.TXT," created Mar. 26, 2012, which is 3 KB in size. The information in the electronic format of the sequence listing is incorporated herein by reference in its entirety.

BACKGROUND OF THE INVENTION

The present invention relates to polymerase chain reaction (PCR) assays for quantification of DNA. More specifically, the invention relates to assays for the real-time quantification of human mitochondrial DNA (mtDNA).

Sequence analysis of human mtDNA has become a valuable forensic tool for specimens, such as hair and calcified tissue samples, in which nuclear DNA analysis may fail due to DNA degradation or insufficient template. Analysis of mtDNA may be possible in such cases because human cells contain hundreds to perhaps thousands of mtDNA copies. In addition, mtDNA is circular and more resistant to exonuclease digestion. However, even though abundant on a cellular basis, mtDNA quantities may be limited. Thus, judicious use of a sample is important so that sample consumption is minimized and amplification of mtDNA template is optimized.

Another important consideration in forensic mtDNA analysis is inhibition of amplification. Hair and calcified tissue may contain PCR inhibitors, such as melanin and humic acid, respectively, at levels that could interfere with PCR and subsequent analysis. Internal positive controls (IPCs) may be used to determine whether a sample contains PCR inhibitors or insufficient template.

Real-time quantitative PCR (qPCR), a highly specific, sensitive, and reproducible method for quantifying nucleic acids, represents an attractive approach to quantifying mtDNA. Using a DNA standard, actual copy numbers of a target sequence in a sample may be determined via qPCR. Optimally, the standard contains a DNA sequence, which is different from, but associated with or linked to, the sequence to be analyzed, to eliminate the risk of contamination by the standard. Human mtDNA forensic analysis involves the non-coding hypervariable regions (HVRs) where most variation in mtDNA is found. The mtDNA coding region also contains sequence variation; therefore it is difficult to generate or identify a mtDNA standard that lacks sequence variation. Nonetheless, the present invention utilizes a unique standard and corresponding target sequence that represents a mtDNA coding sequence containing minimal variation.

The prior art discloses several qPCR assays for quantifying human mtDNA. Many such prior art assays utilize highly specific fluorogenic probes and mtDNA-specific standard curves, which enable the absolute quantification of mtDNA down to 10 copies of mtDNA or less. Other prior art assays are characterized by a high specificity for human DNA and incorporate an IPC to detect PCR inhibitors, which serves to identify those samples that may require additional purification.

The qPCR-based invention described herein combines these features as well as the ability to quantify degraded DNA, high reproducibility, and a wide dynamic range to enable quantification of low copy number samples, such as hair shafts, bone, and degraded blood, as well as high copy number samples, such as fresh blood and buccal swabs. In addition, the present invention utilizes a unique DNA standard that provides quality control and lacks topological constraint, common with plasmid-based standards, thereby allowing for greater accuracy of quantification.

BRIEF SUMMARY OF THE INVENTION

To overcome limitations associated with known assays for mtDNA quantification, the present invention was developed to quantify mtDNA via real-time quantitative PCR (qPCR), based on absolute quantification. The inventive assay exhibits high sensitivity and specificity and a large dynamic range to enable the quantification of as few as ten copies of mtDNA to as many as $10^8$ copies of mtDNA (0.17 fg-1.7 ng of mtDNA, respectively).

In addition, the present invention allows for the quantity and quality of mtDNA in a given biological sample (even a degraded sample) to be determined prior to commencement of forensic mtDNA analysis, which increases the likelihood of successful analysis, improves the efficiency of analysis by indicating the need for sample repurification, and helps conserve sample for additional analyses, if necessary. In one embodiment of the invention, the assay can be used to direct the degree of sample dilution necessary to minimize sample consumption, while ensuring assay success, resulting in a determination of the minimum number of mtDNA copies required for forensic analysis.

In another embodiment of the invention, to ensure optimal quality assurance and quality control, the assay employs a synthetic DNA standard of known quantities to generate a standard curve from which the quantities of mtDNA in sample preparations may be determined. The standard is synthetic, thereby ensuring high quality control between different standard preparations. In addition, the standard includes a signature sequence to distinguish it from naturally existing mtDNA sequences, thereby facilitating its identification if it were to become a contaminant in the forensic laboratory.

In another embodiment of the invention, the qPCR assay focuses on a 105-base pair target sequence. The target sequence is minimally homologous to non-human mtDNA, thereby providing high specificity for human mtDNA.

In another embodiment, the present invention is used to identify whether PCR inhibitors are present in a biological sample at a level that could inhibit the amplification and subsequent analysis of mtDNA in the sample. If PCR inhibitors are identified, then repurification of the sample may be indicated.

BRIEF DESCRIPTION OF THE DRAWINGS

A more complete appreciation of the present invention, and many of the features and advantages of the present invention, will be readily apparent as the same becomes better understood by reference to the following detailed description when considered in conjunction with the accompanying drawings, wherein:

FIG. 7 shows the primer, probe, and standard sequences. The region amplified in the mtDNA qPCR method of an embodiment of the present invention is the NADH dehydrogenase subunit 5 gene of human mtDNA. The positions of the amplification primers are underlined and the probe sequence is capitalized. The standard sequence is shown in bold type. The box indicates the sequence of the standard that was modified to create a signature sequence. The signature sequence contains five nucleotide substitutions, which, if translated, would result in the introduction of a stop codon (Och, ochre) and an amino acid substitution (Arg, arginine), as indicated.

DETAILED DESCRIPTION OF THE INVENTION

Figure 1:
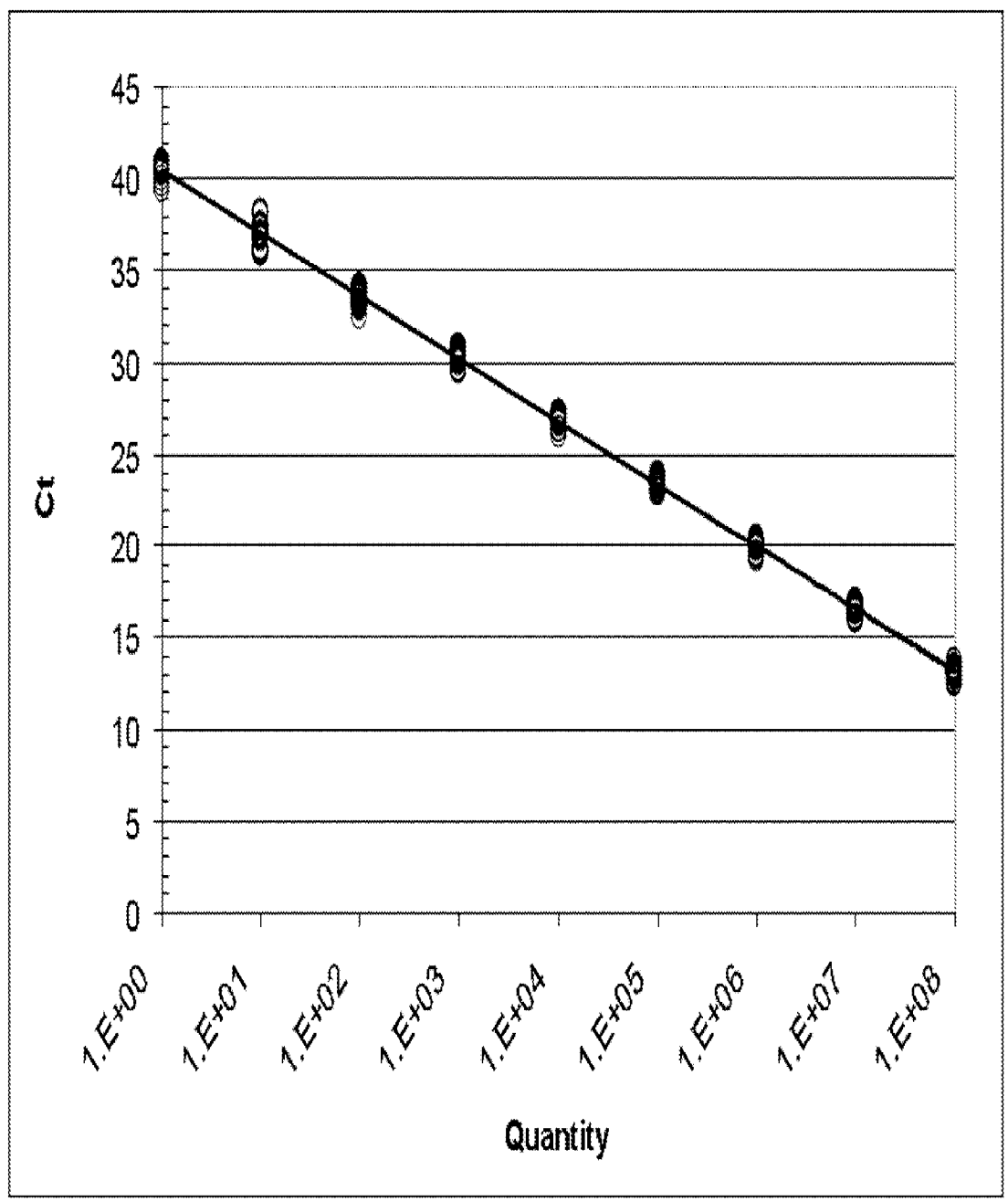
FIG. 1 is a graph showing the reproducibility of the standard curve. The plot represents a compilation of cycle threshold (Ct) data from 15 separate assays in which each standard was assayed in duplicate or more over a 7-month period. Nine of the assays were conducted by one analyst and six of the assays were conducted by a second analyst using a different instrument. The trend line representing the average Ct value among all assays is shown ($R^2=0.9999$). Overall efficiency was calculated to be 96.5% using the slope of the trend line. The ranges for individual standard quantities varied from 0.9 Ct ($10^5$ copies) to 2.3 Ct ($10^1$ copies). Standard quantities of $10^0$ represent Y-intercepts of the trend line for each of the 15 assays.

The invention is directed to real-time quantitative PCR (qPCR) assays to quantify human mtDNA and ensure sufficient quantity and quality exists for subsequent forensic analysis. However, the invention may also be used in the medical, anthropological, and other non-forensic fields. In one embodiment of the invention, the assay is used to quantify human mtDNA by detecting the presence of the NADH dehydrogenase subunit 5 gene in sample DNA preparations.

In a preferred embodiment of the invention, the real-time qPCR assay uses a probe, primers, and a synthetic DNA standard. In a more preferred embodiment, the standard is a unique, linear, duplex, synthetic DNA standard. Benefits of using a synthetic standard include ease of production, high quality control, high purity, low cost (compared to the construction and production of traditional plasmid-based DNA standards), high yield, and rapid production. The inventive standard provides optimal quality assurance and quality control because of its purity and the absence of contaminating DNA, RNA, and protein, which could affect its absorbance of ultraviolet light (260 nm) and result in inaccurate quantification.

In contrast to a linear synthetic standard, experiments involving a plasmid-based standard indicate that DNA supercoiling may result in inefficient amplification and significantly reduced Ct values for the plasmid standard, resulting in a ~50-fold overestimation of copy numbers for samples, which are not supercoiled. This effect could be caused by ineffective annealing of primer and probe due to topological constraints. While this effect may be overcome by nicking or linearization of the plasmid standard followed by repurification, these steps are not required for linear synthetic standards.

Target Sequence

By nature, forensic DNA evidence may contain a mixture of human DNA and contaminating DNA from non-human sources. Furthermore, it can be difficult to determine whether small pieces of recovered skeletal remains are from a human or non-human source. qPCR primers and probes can potentially bind to and amplify non-human mtDNA, resulting in inaccurate yield determinations that may impact downstream analysis. Therefore, one criterion for selecting the qPCR target sequence was low homology with non-human mammalian DNA. Several potential qPCR target regions in the human mtDNA genome were compared to the mtDNA genome sequences of sixteen domesticated and wild mammalian species, which could pose as environmental contaminants, and were evaluated for sequence homology. A sequence within the NADH dehydrogenase subunit 5 gene exhibited relatively low homology with the non-human DNA sequences, and was selected as the qPCR target region for one embodiment of the present invention. Thus, in a preferred embodiment of the invention, the qPCR target region corresponds to positions 13,288-13,392 of the mtDNA revised Cambridge Reference Sequence (NCBI Accession No. NC_012920.1). The small amplicon size (105 bp) facilitates amplification even for degraded DNA.

qPCR Synthetic Standard

The target region contains known single nucleotide polymorphisms (SNP), any of which may be used in forensic analyses pursuant to the present invention. To address the possibility that the qPCR standard could be a potential contaminant in such cases, the qPCR standard, according to one embodiment of the present invention, contains a "signature" or marker sequence at positions 13,345-13,349 of the mtDNA revised Cambridge Reference Sequence (NCBI Accession No. NC_012920.1), representing a change from "GCCAT" to "TAACG" in the forward strand and a change from "atggc" to "cgtta" in the reverse strand. This signature sequence in the forward strand encodes a stop codon (Och, ochre) and a Met (methionine)→Arg (arginine) substitution when translated (FIG. 7), an unlikely occurrence in naturally occurring human mtDNA. The signature sequence, according to another embodiment of the present invention, is located between the probe- and reverse primer-binding sites and does not affect qPCR amplification efficiency. The signature sequence would be readily identified upon sequencing or via a mass spectrometry base composition method.

In one embodiment, the standard also contains five mtDNA base pairs beyond the primer binding sites, which eliminates qPCR quantification inaccuracies that may arise due to undesirable n−1, n−2, etc. oligo products that may be created during oligo synthesis and persist through oligo purification. The standard, containing the mtDNA region amplified (or target sequence) and five additional base pairs on each end, corresponds to positions 13,283-13,397 of the revised Cambridge Reference Sequence (NCBI Accession No. NC_012920.1), except that positions 13,345-13,349 are changed from "GCCAT" to "TAACG."

qPCR Assay

Whereas the exemplary qPCR assay described herein employs a specific protocol and instrument, those of ordinary skill in the art will recognize that it may be easily adapted for any real-time qPCR protocol, instrument, and/or system that can detect 6FAM, VIC, TAMRA, ROX, and other compatible dyes. In addition, the exemplary assay described herein utilizes a "fast" qPCR amplification protocol, which results in a rapid run time of approximately 40 minutes; however, appropriate modifications known to those of ordinary skill in the art may be made to the protocol to carry out "standard" qPCR, e.g., modifications to, for example, the plate, sample block, master mix, and/or cycling parameters.

The qPCR assay of the present invention is suitable for accurate and precise mtDNA quantification in DNA samples prior to forensic analysis and is reliable, robust, and highly sensitive. In addition, the invention may be utilized in biomedical and other applications that demand similar requirements.

EXAMPLES

The examples below are intended to be purely exemplary and are not intended to limit the disclosure or any aspect of the invention.

DNA Samples

The primers and probe of the present invention were designed to specifically amplify human mtDNA. They hybridize to sequences that are minimally variable, maximizing amplification of a variety of polymorphic sequence types. To attain the highest quantification accuracy of human mtDNA in a sample, the non-specific amplification of contaminating non-human DNA should be minimal. However, the possibility does exist that the qPCR primers and probe may non-specifically bind to and amplify non-human DNA, resulting in non-specific amplification. Furthermore, in forensic DNA analysis, human DNA can be contaminated with DNA from domestic pets, farm animals, wildlife, bacteria, or fungi.

To demonstrate specificity of the qPCR assay for human DNA, a standard quantity (100 ng) of DNA from each of twenty mammalian species and from ten other species, including non-mammalian vertebrates, bacteria, and fungi, was tested. The "apparent" copy numbers obtained via the mtDNA qPCR assay for each of the non-human species were compared to the copy number obtained for the same quantity (100 ng) of commercially prepared human DNA and were cited as a percentage of the human DNA copy number. For example, if the qPCR assay were to fully non-specifically amplify a given non-human sample, then the "apparent" copy number obtained for that sample would be equivalent to, or 100% of, the copy number obtained for the known human sample. This approach assumed that all non-human DNA was free of human DNA and vice versa and that the ratio of mtDNA to total DNA was equivalent for all species.

The human (Zyagen GH-180) and other vertebrate DNA samples were purchased from Zyagen Laboratories (10225 Barnes Canyon Road, San Diego, Calif., 92121), and the bacterial and fungal DNA were purchased from the American Type Culture Collection (ATCC) (10801 University Boulevard, Manassas, Va., 20110). The non-human vertebrate DNA included DNA from bovine (Zyagen GB-110), cat (Zyagen GC-130), chicken (Zyagen GC-120), deer (Zyagen GD-140), dog (Zyagen GD-150), donkey (Zyagen GD-160), equine (Zyagen GE-170), ferret (Zyagen GF-180), fish (Zyagen GF-190), gerbil (Zyagen GG-120), goat (Zyagen GG-150), guinea pig (Zyagen GG-160), hamster (Zyagen GH-170), monkey (baboon) (Zyagen GM-140B), monkey (cynomolgus) (Zyagen GM 140C), monkey (rhesus) (Zyagen GM-140R), mouse (Zyagen GM-150), pig (Zyagen GP-160), rabbit (Zyagen GR-170), rat (Zyagen GR-180), sheep (Zyagen GS-190), and turkey (Zyagen GT-150). The bacterial DNA included DNA from *Bacillus subtilis* (ATCC 23857D-5), *Clostridium perfringens* (ATCC 13124D), *Escherichia coli* (ATCC 10798D), *Pseudomonas aeruginosa* (ATCC 17933D), *Staphylococcus epidermidis* (ATCC 12228D), and *Streptococcus pneumoniae* (ATCC BAA-334D). The fungal DNA included DNA from *Aspergillus oryzae* (ATCC 42149D-2) and *Candida albicans* (ATCC 14053D).

The results showed that only slight non-specific amplification was apparent for 19 of the 30 non-human species examined with the greatest for cynomolgus monkey DNA, which was quantified at a level representing less than 1% of the human DNA copy number. At this level, an improbable amount of contaminating cynomolgus monkey DNA, 100-fold more, would be required to attain a signal equivalent to human DNA. Two additional primate species DNA, rhesus monkey and baboon, exhibited cross-reactivity approximately 30- and 90-fold lower than the cynomolgus monkey, respectively. Farm, wildlife, and pet species, often encountered with recovered human remains, were quantified at levels less than or equal to 0.4% that of the human DNA copy number, which demonstrated no appreciable non-specific amplification. Virtually no cross-reactivity was observed among the bacterial and fungal species examined. Given the high specificity of the qPCR assay according to the present invention, human mtDNA quantification should be virtually unaffected by the presence of mtDNA copies of the non-human DNA types listed here. See Table 4.

TABLE 4 qPCR Cross-reactivity with Non-human DNA

| DNA Source | Apparent Copy Number of Human mtDNA per 100 ng of DNA* | % of Human |
|---|---|---|
| Human | 1,900,000 | 100% |
| Cynomolgus Monkey | 18,000 | 0.9% |
| Cow | 7,800 | 0.4% |
| Guinea Pig | 1,200 | 0.1% |
| Rhesus Monkey | 490 | 0.03% |
| Baboon | 140 | 0.01% |

*The following organisms were quantified at 35 copies or less per 100 ng DNA (<0.002% of human): chicken, deer, dog, horse, ferret, fish, gerbil, hamster, mouse, rabbit, rat, sheep, turkey, and C. albicans. mtDNA was not detected in DNA from cat, donkey, goat, pig, A. oryzae, B. subtilis, C. perfringens, E. coli, P. aeruginosa, S. epidermis, and S. pneumonia.

To evaluate the present invention with a "forensic-type" specimen, buccal swab DNA was extracted using an organic extraction method. Briefly, a half buccal swab was incubated at 56° C. for 2 hours in a buffer containing 10 mM Tris, 100 mM NaCl, 39 mM DTT, 10 mM EDTA, 2% SDS, and 1.2 units of proteinase K. The swab was removed and the solution was extracted with an equal volume of phenol/chloroform/isoamyl alcohol (25:24:1, v/v). The aqueous layer was purified using a Microcon 100 centrifugal device (Millipore, Billerica, Mass.). DNA was recovered from the device with 60 µl of water. The samples were stored at −20° C. until experimentation and at 4° C. during the period of experimentation.

qPCR Standard

The dsT8sig qPCR standard consisted of two complementary, PAGE-purified, synthetic oligonucleotides (Ultramers™, Integrated DNA Technologies, Inc., Coralville, Iowa) (Table 1) that correspond to positions 13,283-13,397 of the mtDNA revised Cambridge Reference Sequence (NCBI Accession No. NC_012920.1), i.e., the target sequence (with the signature sequence change) plus five additional base pairs at both the 5' and 3' ends. For quality control, as noted, the forward strand of the standard contained a signature or marker sequence, TAACG, corresponding to positions 13,345-13,349 of the reference sequence and the reverse strand contained the reverse complement, CGTTA, at this position.

TABLE 1

Sequences of DNA Standard, Primers, and Probe qPCR Standard (forward strand)
Tfor8sig: 5'-CAA TCG GCA TCA ACC AAC CAC ACC TAG
CAT TCC TGC ACA TCT GTA CCC ACG CCT TCT TCA AAT
AAC GAC TAT TTA TGT GCT CCG GGT CCA TCA TCC ACA
ACC TTA ACA ATG AAC A-3' [SEQ ID NO: 1]

qPCR Standard (reverse strand)
Trev8sig: 5'-TGT TCA TTG TTA AGG TTG TGG ATG ATG
GAC CCG GAG CAC ATA AAT AGT CGT TAT TTG AAG AAG
GCG TGG GTA CAG ATG TGC AGG AAT GCT AGG TGT GGT
TGG TTG ATG CCG ATT G-3' [SEQ ID NO: 2]

Forward Primer
Qfor8: 5'-GGC ATC AAC CAA CCA CAC CTA-3'
[SEQ ID NO: 3]

Reverse Primer
Qrev8: 5'-ATT GTT AAG GTT GTG GAT GAT GGA-3'
[SEQ ID NO: 4]

TABLE 1-continued

Sequences of DNA Standard, Primers, and Probe

Probe (MGBNFQ = minor groove binder
nonfluorescent quencher)
QRL8: 5'-6FAM CAT TCC TGC ACA TCT G MGBNFQ-3'
[SEQ ID NO: 5]

Figure 8:
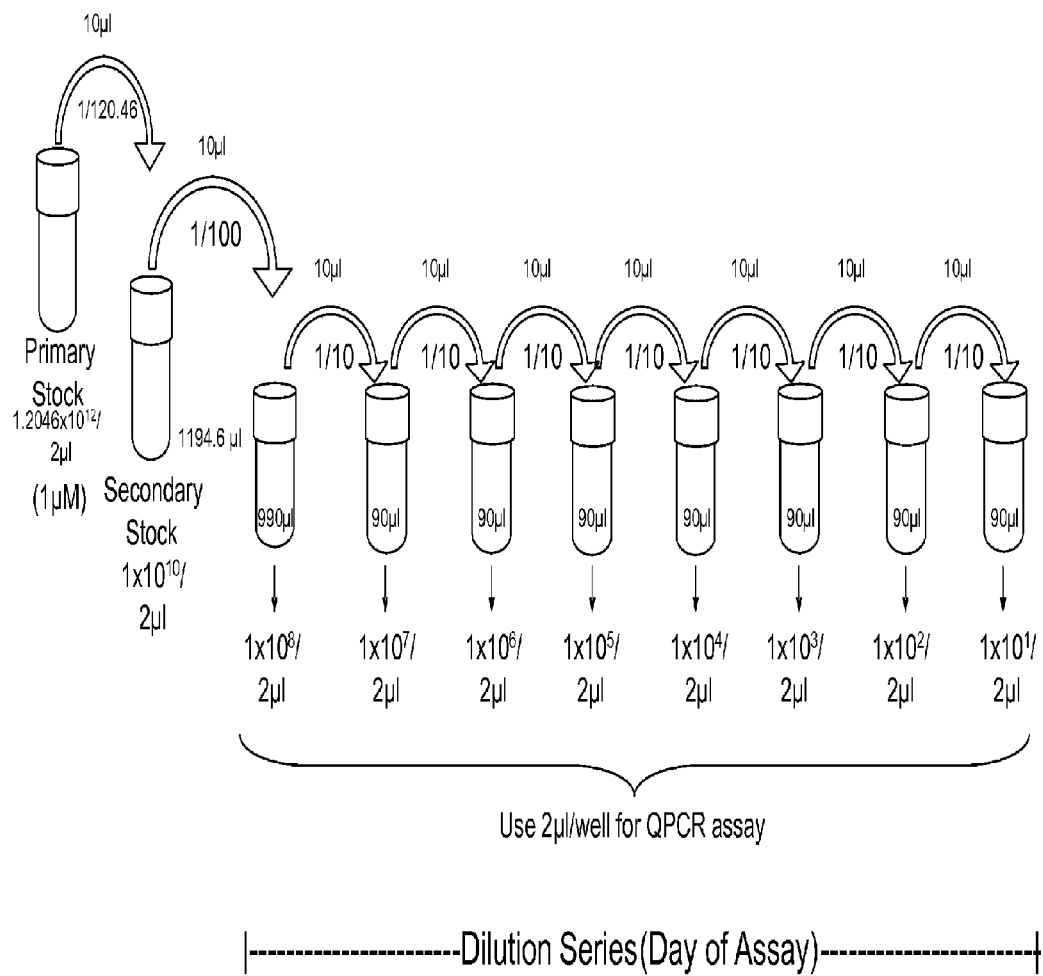
FIG. 8 is an exemplary dilution series for the preparation of the synthetic dsT8sig standards.

The forward and reverse qPCR standard oligonucleotides were separately reconstituted in Tris EDTA (TE) buffer (10 mM Tris-HCl, pH 8.0, 0.1 mM EDTA) and quantified by measuring their absorbance of ultraviolet light at a wavelength of 260 nm and applying the extinction coefficients 1,082,000 and 1,138,100 L/(mole·cm), respectively. The concentration of each oligonucleotide was then adjusted to 2 µM and the adjusted oligonucleotides were mixed in equal proportions to generate a 1 µM double-stranded, primary qPCR standard stock. The primary stock was diluted with TE buffer to generate a secondary standard stock containing $10^{10}$ copies of standard per 2 µl. Primary and secondary standards were aliquoted (10 µl) and stored at −80° C. The assay dilution series was prepared fresh daily. The secondary stock was diluted serially with TE buffer to generate the following assay dilution series: $10^8$, $10^7$, $10^6$, $10^5$, $10^4$, $10^3$, $10^2$, and $10^1$ copies per 2 µl (FIG. 8).

Figure 9:
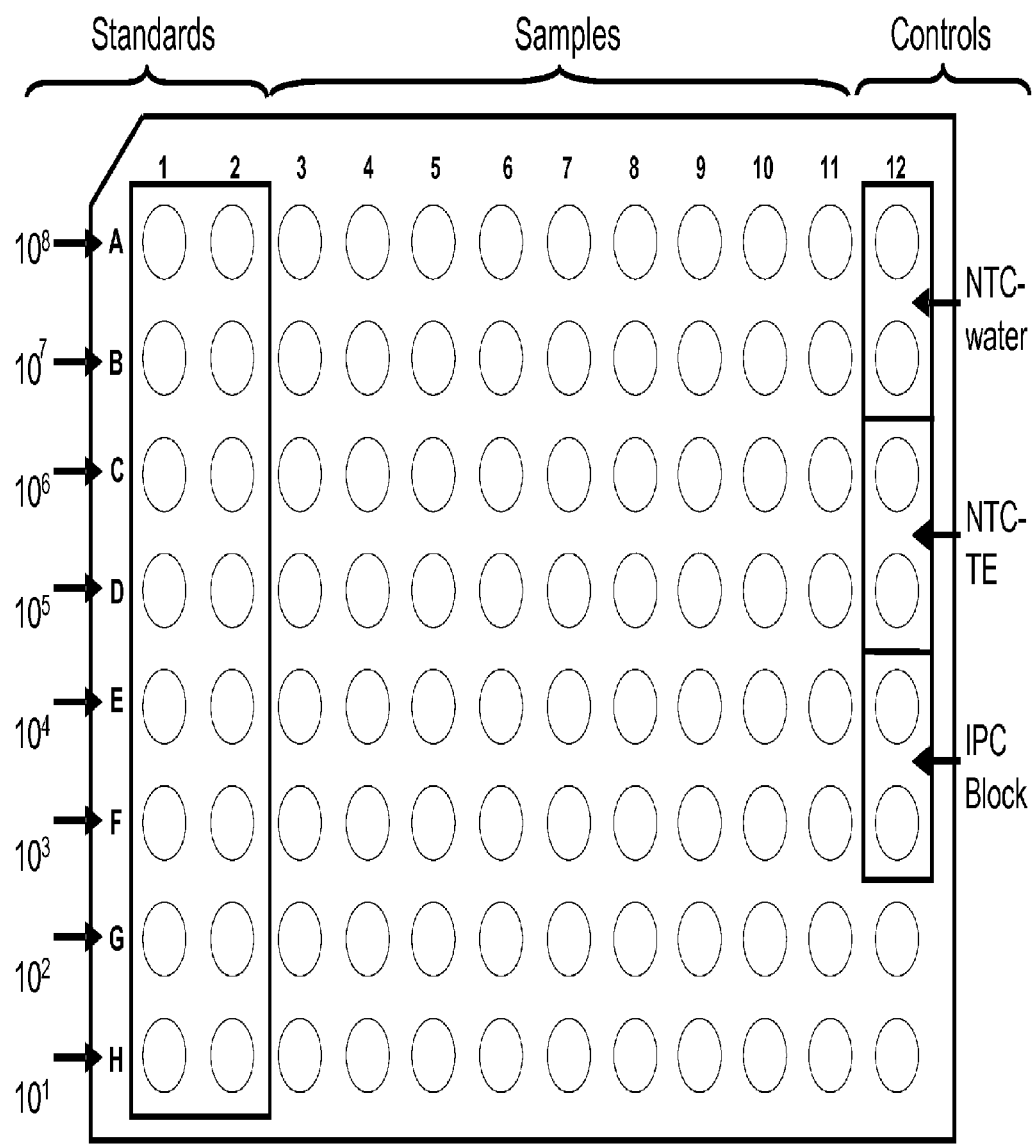
FIG. 9 is an exemplary qPCR plate layout according to an embodiment of the invention.

Real-time qPCR qPCR experiments were conducted with 2 µl of sample DNA, standard DNA, or control reagents (described below) per well of a 96-well plate in a 25 µl duplex reaction containing 12.5 µl of TaqMan 2× Fast Universal Master Mix (no UNG) (Applied Biosystems, Foster City, Calif.), 900 nM HPLC-purified forward and reverse primers (SEQ ID NOS: 3 and 4, respectively) (Integrated DNA Technologies, Inc.), and 250 nM HPLC-purified 5' 6FAM-labeled probe containing a 3' minor groove binder nonfluorescent quencher (SEQ ID NO: 5) (Applied Biosystems). The qPCR reaction also included the TaqMan Exogenous Internal Positive Control Reagents (Applied Biosystems) according to the manufacturer's recommendations, except for the blocking reagent, which, in the control wells, contained the Exogenous IPC Blocking Reagent at a final concentration of 0.8× instead of the recommended 1×. Additional control reactions consisted of water NTCs (no template controls) and TE NTCs. See FIG. 9.

Reactions were amplified in duplicate, unless otherwise noted, on a 7900HT FAST Sequence Detection System (Applied Biosystems) in "fast" mode: 20 seconds at 95° C. followed by 40 cycles of 1 second at 95° C. and 20 seconds at 60° C. Data were analyzed for both mtDNA- and IPC-specific probes with Sequence Detection Software (SDS) version 2.2.2 (Applied Biosystems). Cycle threshold (Ct) values were determined at 0.2 ΔRn using the automatic baseline algorithm. qPCR amplification efficiencies were calculated using the slope of the standard plot regression line: efficiency=$[10^{(-1/slope)}]-1$.

Exogenous IPC Analysis

In another embodiment of the present invention, amplification of an IPC is used to determine whether PCR inhibitors are present in a DNA sample. The amplification involves inclusion of IPC-specific primers and probe in the qPCR reaction mixture as well as IPC DNA, which is expected to amplify in the absence of PCR inhibitors. The highest level of IPC amplification, and therefore the lowest IPC Ct values, is expected for the NTC controls that lack PCR inhibitors. In contrast, in the presence of inhibitors, IPC Ct values should increase relative to that for the NTCs or be "undetermined," for low levels and high levels of inhibitor, respectively.

Figure 4:
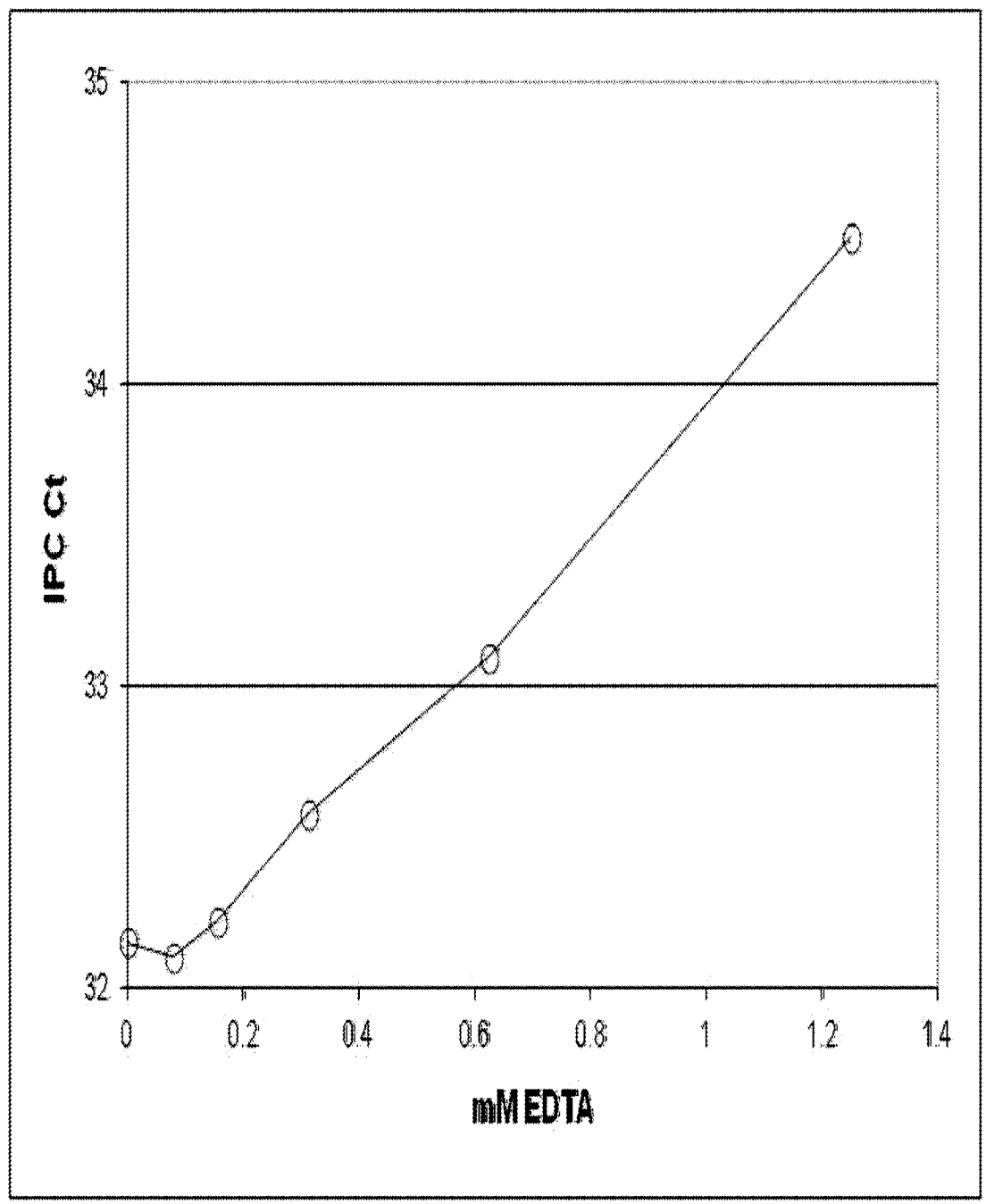
FIG. 4 shows inhibition of an internal positive control (IPC) signal by ethylenediaminetetraacetic acid (EDTA). A stock EDTA solution was two-fold serially diluted and added to wells in quadruplicate to yield final concentrations ranging from 10 to 0.078 mM. Average Ct values are shown. Ct values for final EDTA concentrations ≥2.5 mM were undetermined.

Specifically, a controlled inhibition experiment was conducted using two-fold serial dilutions of EDTA varying in final concentration from 10 to 0.078 mM per well. The qualitative analysis with EDTA as inhibitor (FIG. 4) revealed that 0.078 mM EDTA yielded a Ct value comparable to the Ct value for the NTC (0 mM EDTA), thus indicating a lack of inhibition. In contrast, a slight increase in Ct, e.g., 0.31 mM EDTA, indicated low level inhibition, a marked increase in Ct, e.g., 1.25 mM EDTA, indicated a moderate level of inhibition, and an "undetermined" Ct, e.g., ≥2.5 mM EDTA, suggested a potentially high level of inhibition. A similar response was observed using the exogenous IPC blocking reagent as inhibitor although at concentrations specific for that inhibitor. Thus, uninhibited samples were defined as those which had IPC Ct values comparable to that of the NTCs within a given assay, whereas highly inhibited samples had "undetermined" Cts. Partially inhibited samples were defined as those having Cts higher than the NTCs.

Figure 5:
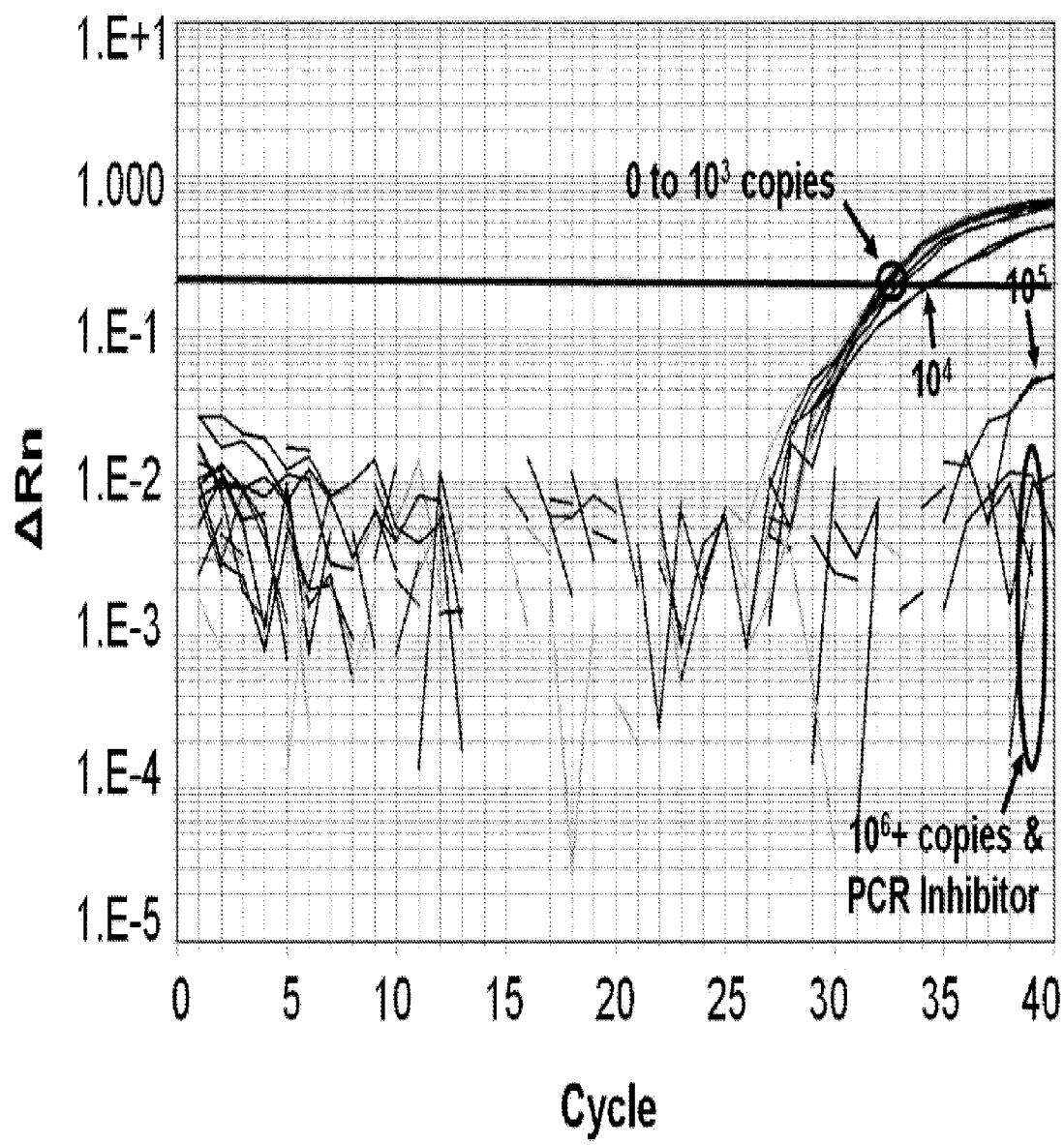
FIG. 5 shows an amplification plot for the exogenous internal positive control (IPC) for the qPCR standard and controls according to an embodiment of the present invention. The plot illustrates that the lowest IPC Ct values are obtained from zero copies, that is "no template" controls, to $10^3$ copies of standard per well. However, IPC amplification is completely inhibited in the presence of PCR inhibitor, e.g., IPC blocking reagent, or when ≥$10^5$ copies of qPCR standard are present in a well, the latter representing "inhibition by competition." $10^4$ copies of the standard also inhibit IPC amplification by this mechanism, though only slightly. The bold horizontal line depicts the 0.2 ΔRn threshold.

IPC Ct values can also increase in the absence of inhibitors when high levels of sample mtDNA compete for polymerase and dNTPs during amplification, termed "inhibition by competition." This phenomenon is readily observed with the inhibitor-free standards where the IPC Ct is slightly increased with $10^4$ mtDNA standard copies per well (FIG. 5). At $10^5$ copies of standard, the IPC Ct becomes "undetermined" and at $10^6$ copies, IPC amplification appears indistinguishable from the background fluorescent signal. Inhibition by competition is an unavoidable consequence of the relatively low quantities of IPC DNA within the qPCR reaction mixture. Nonetheless, IPC analysis is informative and remains valid for any sample that contains ≤$10^4$ copies of mtDNA per well. Detection of inhibition in such samples suggests that further sample purification might be warranted. For samples that contain >$10^4$ copies of mtDNA per well, no determination may be made regarding the presence of PCR inhibitors; however, given the successful qPCR amplification of and high level of mtDNA in such samples, inhibitors, if present, are not expected to cause interference with downstream forensic mtDNA analysis.

mtDNA Hypervariable Region (HVR) PCR

An important benefit of the assay of the present invention is the conservation of forensic DNA samples to allow for additional analysis. In this regard, the assay described herein can be used to determine the optimum number of mtDNA copies needed for HVR amplification.

To determine the optimal quantity of human mtDNA needed for down-stream forensic analysis, ten-fold serial dilutions of human DNA (Zyagen Laboratories, GH-180) were subjected to HVR amplification in duplicate as follows. Hypervariable region 1 (HVR1) amplification: 10 μl of DNA in a reaction mixture containing 5 units AmpliTaq Gold DNA polymerase (Applied Biosystems), 1× GeneAmp PCR buffer (Applied Biosystems), 160 ng/μl BSA (#A3550, Sigma-Aldrich, St. Louis, Mo.), dNTP mixture (dATP, dCTP, dGTP, and dTTP, 250 μM each), 600 nM forward primer CAC CAT TAG CAC CCA AAG CT [SEQ ID NO: 6], and 600 nM reverse primer GAG GAT GGT GGT CAA GGG AC [SEQ ID NO: 7]. Hypervariable region 2 (HVR2) amplification reaction mixtures were similar, except for the forward primer, CTC ACG GGA GCT CTC CAT GC [SEQ ID NO: 8], and the reverse primer, CTG TTA AAA GTG CAT ACC GCC [SEQ ID NO: 9]. Reaction mixtures were amplified using a 95° C. hold for 9 minutes; 32 cycles consisting of 95° C. for 10 seconds, 60° C. for 30 seconds, and 72° C. for 30 seconds; and a 4° C. hold. Amplicons were quantified with the Agilent DNA 1000 kit (Agilent Technologies, Waldbronn, Germany).

Figure 6:
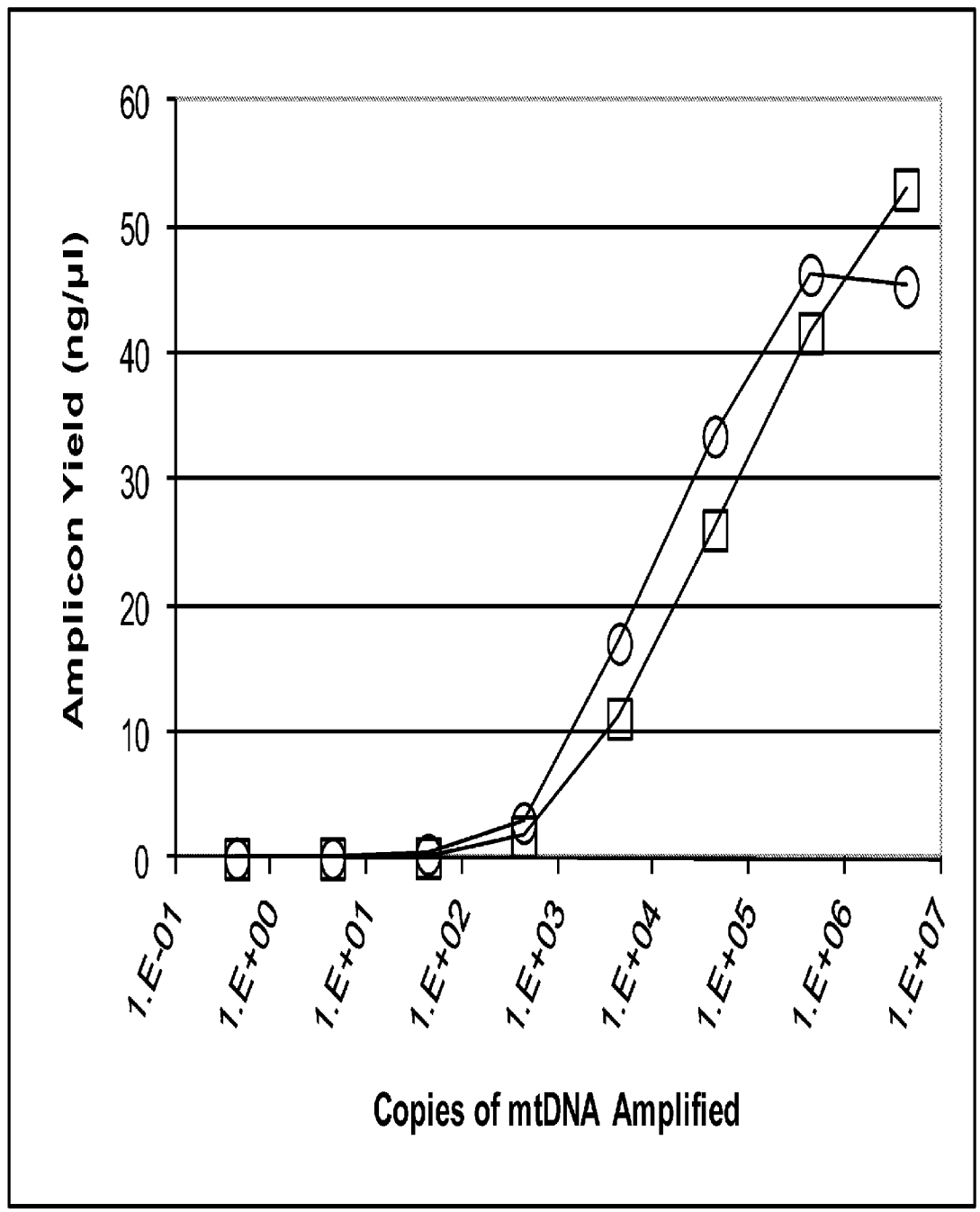
FIG. 6 shows hypervariable region (HVR) amplicon yield from mtDNA using the qPCR assay according to an embodiment of the present invention. A commercially available human genomic DNA preparation was quantified using an embodiment of the qPCR assay, and dilutions of the preparation were subjected to HVR1 (circles) and HVR2 (squares) amplification in duplicate. Duplicate values were consistent with each other and average values were plotted.

The results revealed that 10 pg of human genomic DNA (440 mtDNA copies) subjected to HVR1 and HVR2 amplification yielded 3 ng/μl and 2 ng/μl of amplicon, respectively, concentrations that are sufficient for sequence analysis (FIG. 6). These results were corroborated using HL60 cell line DNA (ATCC, #CCL-240D) in which 180 copies (1 μg) yielded 2 ng/μl and 1 ng/μl of amplicon, respectively. Based on these data, ~300 copies of mtDNA may be sufficient for HVR1 and HVR2 amplification and subsequent forensic analysis. This amount of mtDNA also approximates the number of mtDNA copies present within a single healthy human cell, suggesting that forensic mtDNA analysis may be possible on the total DNA from a single cell, assuming 100% extraction efficiency, the absence of DNA degradation, and the absence of PCR inhibitors. The number of mtDNA copies required for analysis may be substantially higher for DNA isolated from sub-optimal forensic specimens. Nonetheless, the described results support a rational dilution scheme for forensic mtDNA and demonstrate the utility of mtDNA-specific qPCR according to the present invention for sample conservation.

Assay Sensitivity and Reproducibility

Data generated for the highly purified synthetic standard demonstrated consistently high assay sensitivity and reproducibility. Among fifteen individual assays, 100,000,000 ($10^8$) copies of the highly purified standard per well exhibited an average Ct of 13.2 (range 12.5-13.7). The subsequent 10-fold dilution ($10^7$/well) exhibited a Ct value of 16.6 (range 15.9-17.0). The difference in Ct values between each successive dilution of the standard averaged about 3.4 cycles. Ten copies of standard per well were always detected at an average Ct of 37.0 (range 35.9 - 38.2), well within the 40 cycles prescribed for the assay.

High consistency of results and assay reproducibility were also demonstrated by compiling the standard curve results from the 15 separate assays (FIG. 1; Table 2; Table 3). Furthermore, these assays were conducted over a seven month period, thereby demonstrating high stability of the qPCR standard when stored as aliquots at −80° C. In addition, these assays were performed by two different analysts on separate instruments, demonstrating that the assay is highly robust. Of note, mtDNA quantities calculated for a theoretical sample using the linear regression data sets revealed high reproducibility of quantification, yielding a coefficient of variation (CV) of 17% among the 15 different assays. These results may be attributable to consistently high amplification efficiencies, which ranged from 94.5 to 100.2%. Although consistent Ct values were observed for each dilution of the qPCR standard, variation in instrument optics and/or reagents, e.g., probe dye brightness, may cause Ct values to vary. However, in the absence of such variation, consistent standard Ct values specific to the instrument and reagents should be obtained.

TABLE 2

Standard Ct Data for Fifteen Separate qPCR Assays

| Copies/well | Average | Minimum | Maximum | Range |
|---|---|---|---|---|
| $10^8$ | 13.2 | 12.5 | 13.7 | 1.2 |
| $10^7$ | 16.6 | 15.9 | 17.0 | 1.1 |
| $10^6$ | 20.0 | 19.3 | 20.4 | 1.1 |

TABLE 2-continued

Standard Ct Data for Fifteen Separate qPCR Assays

| Copies/well | Average | Minimum | Maximum | Range |
|---|---|---|---|---|
| $10^5$ | 23.5 | 22.9 | 23.9 | 0.9 |
| $10^4$ | 26.9 | 26.1 | 27.3 | 1.2 |
| $10^3$ | 30.4 | 29.5 | 30.9 | 1.5 |
| $10^2$ | 33.6 | 32.4 | 34.1 | 1.7 |
| $10^1$ | 37.0 | 35.9 | 38.2 | 2.3 |
| $10^{0*}$ | 40.5 | 39.5 | 41.0 | 1.5 |

*Represents Y-intercept data

TABLE 3

Linear Regression Data for Fifteen Separate qPCR Assays

| Run | Slope | Y-Intercept | $R^2$ | Efficiency | Calc. Qty.* |
|---|---|---|---|---|---|
| 1 | −3.35 | 39.49 | 1.000 | 98.7% | 6.49E+05 |
| 2 | −3.41 | 39.98 | 1.000 | 96.4% | 7.25E+05 |
| 3 | −3.43 | 40.58 | 0.999 | 95.9% | 1.02E+06 |
| 4 | −3.40 | 40.33 | 0.999 | 96.9% | 9.65E+05 |
| 5 | −3.42 | 40.48 | 1.000 | 96.0% | 9.70E+05 |
| 6 | −3.32 | 39.77 | 0.999 | 100.2% | 9.13E+05 |
| 7 | −3.43 | 40.78 | 0.999 | 95.5% | 1.13E+06 |
| 8 | −3.39 | 40.54 | 0.997 | 97.2% | 1.15E+06 |
| 9 | −3.36 | 40.61 | 1.000 | 98.3% | 1.34E+06 |
| 10 | −3.44 | 40.79 | 0.999 | 95.1% | 1.08E+06 |
| 11 | −3.45 | 40.73 | 0.998 | 94.7% | 9.99E+05 |
| 12 | −3.41 | 40.68 | 1.000 | 96.3% | 1.14E+06 |
| 13 | −3.39 | 40.58 | 0.998 | 97.3% | 1.19E+06 |
| 14 | −3.46 | 40.92 | 1.000 | 94.7% | 1.13E+06 |
| 15 | −3.46 | 40.99 | 1.000 | 94.5% | 1.15E+06 |
| Average | −3.41 | 40.48 | 0.999 | 96.5% | 1.0E+06 |
| Standard Deviation | 0.04 | 0.42 | 0.001 | 1.6% | 1.8E+05 |
| Coefficient of Variation | 0.012 | 0.010 | 0.001 | 0.017 | 0.171 |
| Minimum | −3.46 | 39.49 | 0.997 | 94.5% | 6.49E+05 |
| Maximum | −3.32 | 40.99 | 1.000 | 100.2% | 1.34E+06 |
| Range | 0.14 | 1.50 | 0.003 | 5.7% | 6.87E+05 |

*mtDNA quantity calculated for a theoretical sample exhibiting a Ct value of 20.0, which corresponds to the average Ct for $10^6$ copies of standard.

Figure 2:
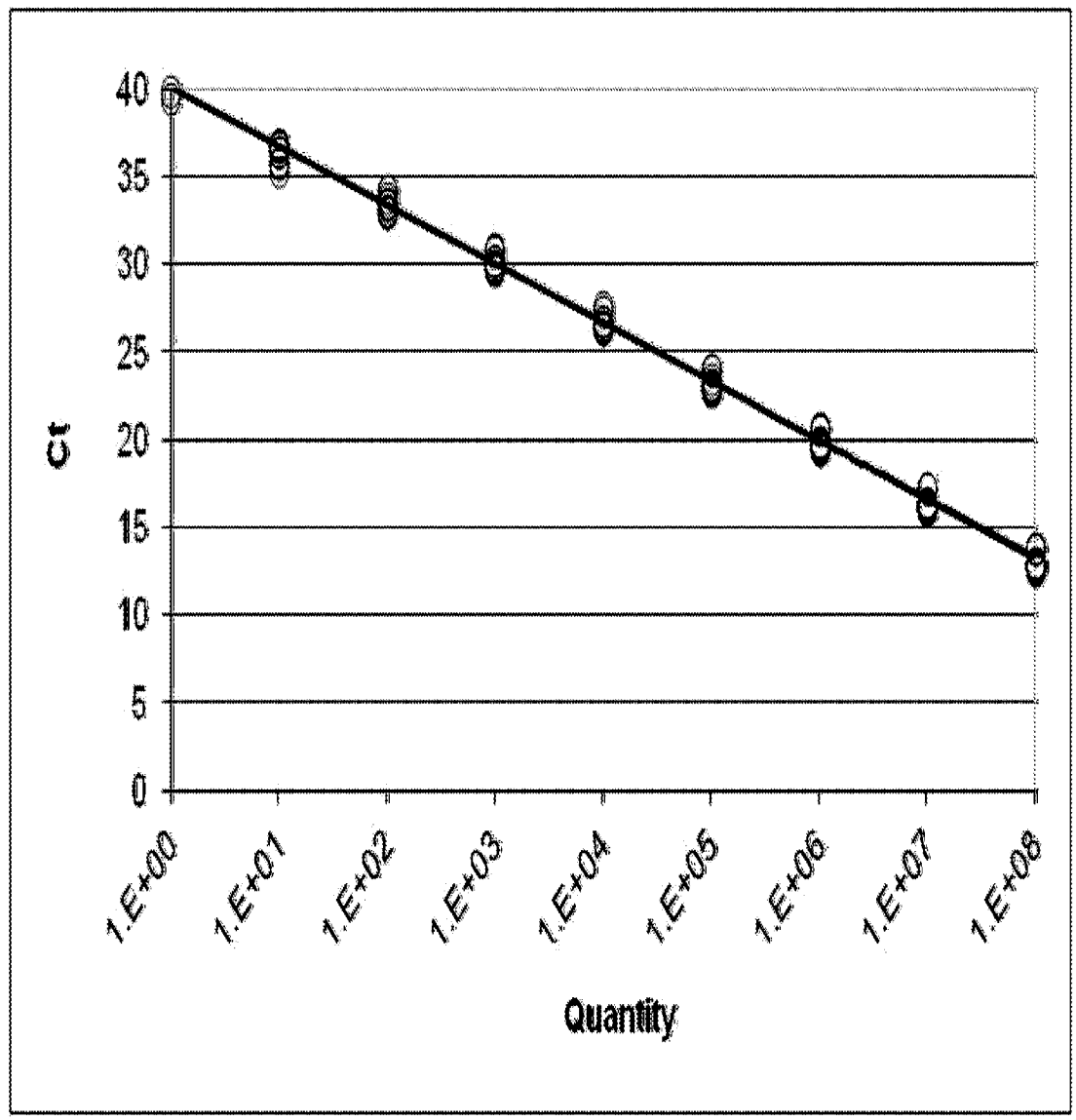
FIG. 2 is a graph showing consistency among different qPCR standard lots. Four different lots of synthetic standard were prepared and subjected to qPCR in duplicate, and a standard curve plot consisting of all lots was generated ($R^2=0.9960$; efficiency=98.6%). The ranges for individual standard quantities varied from 1.2 Ct ($10^3$ copies) to 1.5 Ct ($10^1$ copies). Standard quantities of $10^0$ represent the Y-intercepts of the trend line for each of the four standards.

To examine whether similar assay results would be obtained using different lots of the qPCR standard, three additional sets of the synthetic oligos were obtained and new standard lots were prepared for each set. The four lots of qPCR standard, which included the original lot, were subjected to qPCR and a standard curve plot that consisted of all four lots combined was constructed (FIG. 2). These results revealed consistent Ct values among all lots, thereby demonstrating the reliability of the qPCR standard preparations.

Figure 3:
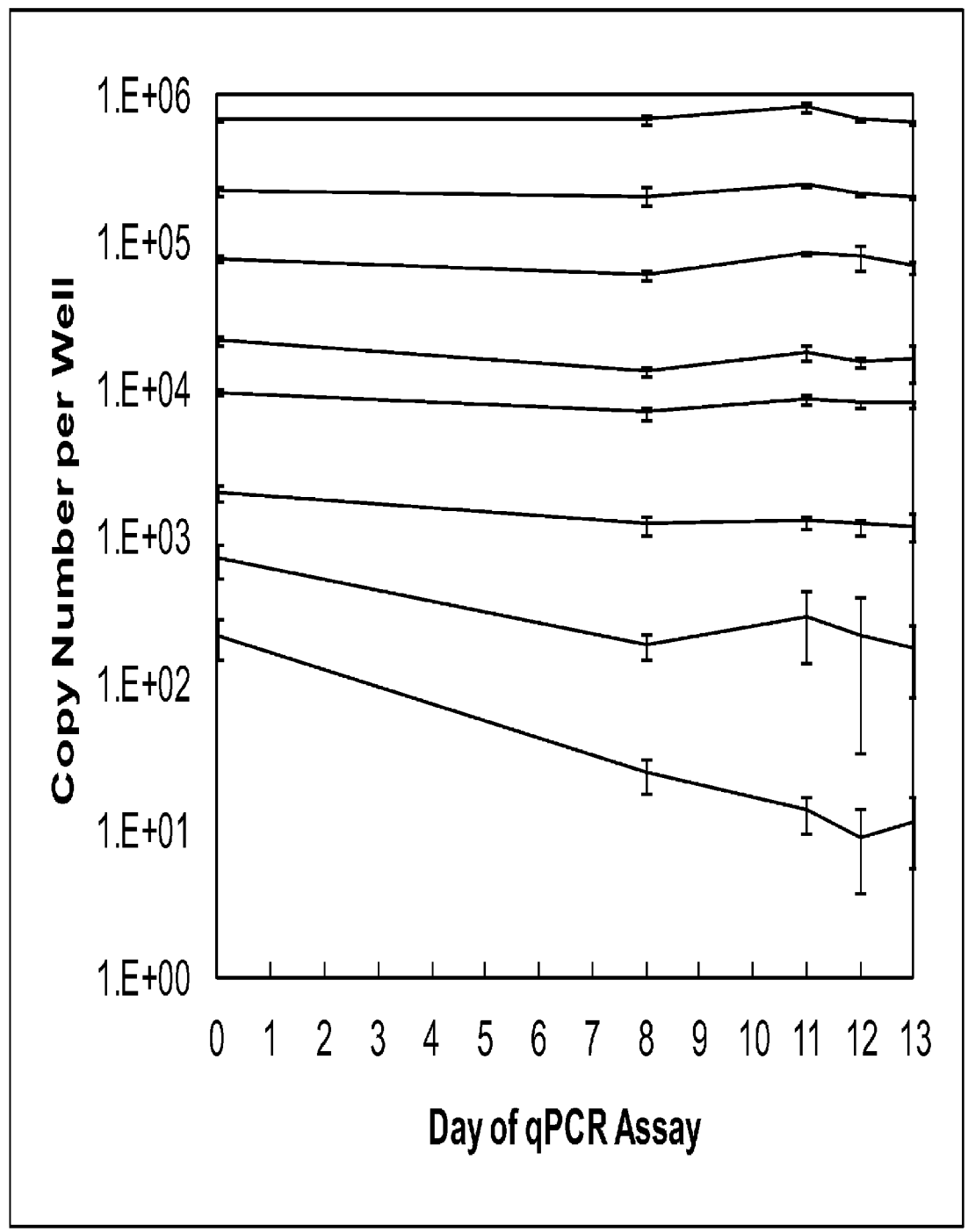
FIG. 3 shows mtDNA quantification of DNA extracts using eight different dilutions (1/2.5-1/13,000) of a buccal swab extract, which were subjected to qPCR (day 0) according to an embodiment of the present invention. The dilutions were subjected to qPCR again after 8, 11, 12, and 13 days of refrigerated storage. Each line represents the results for a single dilution; top to bottom represents the smallest to highest dilution, respectively. Error bars represent the standard deviation of the eight replicates.

Finally, assay reproducibility was verified for an evidentiary type specimen. Various dilutions of a buccal swab DNA extract were assayed five times over a thirteen day period and the results demonstrated high consistency of data, both within assays and between assays, for most dilutions (FIG. 3). Only those dilutions that initially quantified below 1,000 copies displayed higher variability among replicates suggesting mtDNA instability or binding to the inner surface of the storage tube following refrigerated storage of such low copy number samples. The results obtained for this buccal swab extract indicated a mtDNA yield of $2 \times 10^8$ mtDNA copies per swab. However, variation among individuals and differences in swab collection techniques may affect yield.

We claim:
1. An oligonucleotide standard adapted for an assay for quantification of human mitochondrial DNA, said standard comprising: SEQ ID NO: 1 (forward) and SEQ ID NO: 2 (reverse).

* * * * *